(12) United States Patent
Pruett (10) Patent No.: US 10,376,340 B2
(45) Date of Patent: Aug. 13, 2019

(54) DENTAL DEVICE FOR DISPENSING AND WORKING A DENTAL COMPOSITION

(71) Applicant: Fishtech Inc., Colorado Springs, CO (US)

(72) Inventor: Nicolas R. Pruett, Colorado Springs, CO (US)

(73) Assignee: FISHTECH INC., Colorado Springs, CO (US)

(*) Notice: Subject to any disclaimer, the term of this patent is extended or adjusted under 35 U.S.C. 154(b) by 104 days.

(21) Appl. No.: 15/789,430

(22) Filed: Oct. 20, 2017

(65) Prior Publication Data

US 2018/0110587 A1 Apr. 26, 2018

Related U.S. Application Data (60) Provisional application No. 62/410,820, filed on Oct. 20, 2016.

(51) Int. Cl.
| | |
|---|---|
| *A61C 5/00* | (2017.01) |
| *A61C 13/15* | (2006.01) |
| *A61C 3/08* | (2006.01) |
| *A61C 5/62* | (2017.01) |
| *A61C 5/66* | (2017.01) |

(52) U.S. Cl.
CPC ............... *A61C 5/00* (2013.01); *A61C 3/08* (2013.01); *A61C 5/62* (2017.02); *A61C 5/66* (2017.02); *A61C 19/004* (2013.01)

(58) Field of Classification Search
CPC .... A61C 5/00; A61C 5/66; A61C 5/62; A61C 19/004; A61C 3/08

USPC .................................................... 433/80–90
See application file for complete search history.

(56) References Cited

U.S. PATENT DOCUMENTS

| | | | |
|---|---|---|---|
| 3,364,577 A * | 1/1968 | Oakleaf | A61C 13/0028 219/229 |
| 3,900,954 A | 8/1975 | Dragan | |
| 4,391,590 A * | 7/1983 | Dougherty | A61C 9/0026 433/90 |
| 4,643,677 A | 2/1987 | Kim | |
| 4,767,326 A | 8/1988 | Bennett et al. | |
| 4,969,816 A * | 11/1990 | Drumm | A61C 5/66 433/90 |
| 5,129,825 A | 7/1992 | Discko | |
| 5,322,440 A | 6/1994 | Steele | |
| 5,387,103 A | 2/1995 | Fischer | |
| 5,460,523 A * | 10/1995 | Schulman | A61C 5/66 433/90 |
| 5,816,804 A | 10/1998 | Fischer | |
| 6,135,771 A | 10/2000 | Dragan et al. | |
| 6,202,897 B1 * | 3/2001 | Martin | B05C 17/00593 206/269 |
| 6,425,704 B2 | 7/2002 | Voiers et al. | |

(Continued)

FOREIGN PATENT DOCUMENTS

| | | |
|---|---|---|
| EP | 1277446 | 10/2008 |
| WO | WO2012/150471 | 11/2012 |
| WO | WO2014/093926 | 6/2014 |

*Primary Examiner* — Matthew M Nelson
(74) *Attorney, Agent, or Firm* — Alpine IP, PLLC (57) ABSTRACT

Disclosed is a dental carpule with that includes a nozzle for dispensing a dental composition and a burnisher for burnishing the dispensed composition. The carpule allows burnishing a dental composition with the same device used to dispense the dental composition.

21 Claims, 4 Drawing Sheets

(56) References Cited

U.S. PATENT DOCUMENTS

| | | | |
|---|---|---|---|
| 6,585,511 B2* | 7/2003 | Dragan | B05C 17/00593 |
| | | | 401/176 |
| 7,478,736 B2 | 1/2009 | Morgan | |
| 2003/0186195 A1* | 10/2003 | Comfort | A61C 3/08 |
| | | | 433/164 |
| 2004/0091839 A1 | 5/2004 | Fischer | |
| 2005/0244784 A1* | 11/2005 | Dragan | B05C 17/00593 |
| | | | 433/90 |
| 2006/0013637 A1 | 1/2006 | Lemchen | |
| 2011/0117518 A1 | 5/2011 | Pond | |
| 2012/0115103 A1 | 5/2012 | Pauser et al. | |
| 2013/0209158 A1 | 8/2013 | Ziadeh et al. | |
| 2015/0374459 A1* | 12/2015 | Essler | B29C 45/16 |
| | | | 433/89 |

\* cited by examiner

DENTAL DEVICE FOR DISPENSING AND WORKING A DENTAL COMPOSITION

CROSS-REFERENCE TO RELATED APPLICATIONS

This application hereby claims priority to U.S. Provisional Patent Application Ser. 62/410,820, entitled DENTAL DEVICE FOR DISPENSING AND WORKING A DENTAL COMPOSITION, and filed Oct. 20, 2016. The aforementioned application is incorporated herein in its entirety by this reference.

BACKGROUND

1. Field of the Invention

The present invention relates to a dental device and method used to dispense and work a dental composition.

2. Related Technology

A dental practitioner repairs a dental carry in a tooth by first removing decayed tissue and then placing a dental composition (e.g., a dental composite) in the void where the decayed tissue was removed. The majority of dental composites are stored in and dispensed from single use carpules. The carpule is mounted to a syringe gun that extrudes the composite materials from the carpule into the tooth. The carpule has an elongated dispensing nozzle that makes it easy for the dental practitioner to extrude the composition into the prepared restoration site.

After placement of the composite, a dental tool known as a burnisher is used to remove excess composition and spread, pack, contour, and/or shape the dental composite. This burnishing work is necessary for proper bonding, shape, and texturing of the restoration.

SUMMARY

The present invention relates to a dental device for dispensing and working a dental composition. The dental device includes a carpule that has both a dispensing nozzle and an burnisher. The nozzle has a proximal end in fluid communication with a syringe barrel and a distal end configured to dispense the dental composition into a tooth. The burnisher has an elongated shank with a working end configured to work the dispensed dental composition (e.g., compact, remove, shape, etc.). The shank of the burnisher extends separate from the distal end of the nozzle. At least a portion of the burnisher extends adjacent to the nozzle so as to provide a gap between the distal end of the dispensing nozzle and the working surface of the burnisher.

Integrating the burnisher into the carpule allows the dental practitioner to easily position and use the burnisher immediately after dispensing the composite. Instead of removing the carpule from the patient's mouth and inserting a separate burnisher, the carpule is easily rotated or otherwise positioned to use the burnisher instead of the dispensing nozzle.

The nozzle and burnisher are positioned on the carpule and/or separated by a gap distance that allows the practitioner to utilize the burnisher instead of the nozzle without the nozzle interfering with burnishing. The oral cavity is limited in size so properly positioning the burnisher relative to the dispensing nozzle can be important to allow both tools to be utilized within the small space. In some embodiments, the gap between the distal end of the burnisher and the distal end of the nozzle is at least 5, 7, or 9 mm and/or less than 20, 16, or 12 mm, or within a range of any of the foregoing endpoints.

Because the burnisher and nozzle extend separately from the body of the carpule, the distal end of the nozzle and burnisher can be independently optimized. The nozzle may be optimally configured for dispensing the composite and the burnisher may be optimally configured for working the dispensed composition.

Eliminating the need to exchange instruments is particularly advantageous immediately after placing the composite. Dental composites are made to rapidly cure and the quality of the restoration depends in part on the timing of the burnishing during the curing process. The integrated burnisher gives the practitioner flexibility to monitor and/or immediately work the dental composition. If the dental composition cures prematurely, without adequate burnishing, bonding between the composition and the tooth can be compromised.

The time required to exchange a conventional syringe and conventional burnisher can also increase the risk of the restoration site being in contact with the patient's salvia or moisture from the oral cavity. Moisture or saliva contacting the composition before burnishing can cause inadequate bonding of dental composition to the tooth structure.

The integration of the burnisher into the dental syringe can also have benefits related to the operation of the dental practice. For instance, the integrated instruments reduce staff efforts for handling, storing, cleaning, packaging, and/or maintaining inventory of two separate instruments. In some embodiments, the burnisher may be removably connected so that different types of burnishers can be connected to the carpule as needed.

These and other features and benefits of the present invention will become more fully apparent from the following description and appended claims.

DETAILED DESCRIPTION

Figure 1:
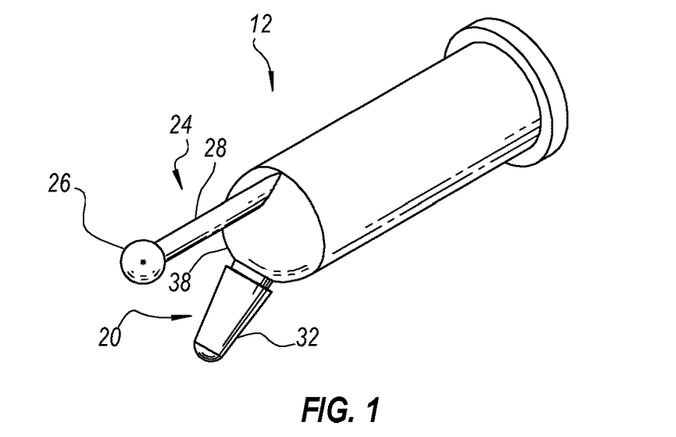
FIG. 1 illustrates a perspective view of a carpule for dispensing and burnishing a dental composition.
Figure 2:
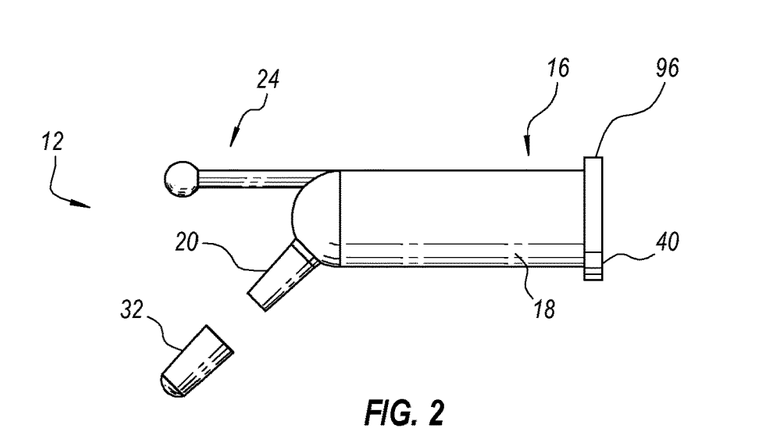
FIG. 2 is an elevational view of the carpule of FIG. 1.
Figure 3:
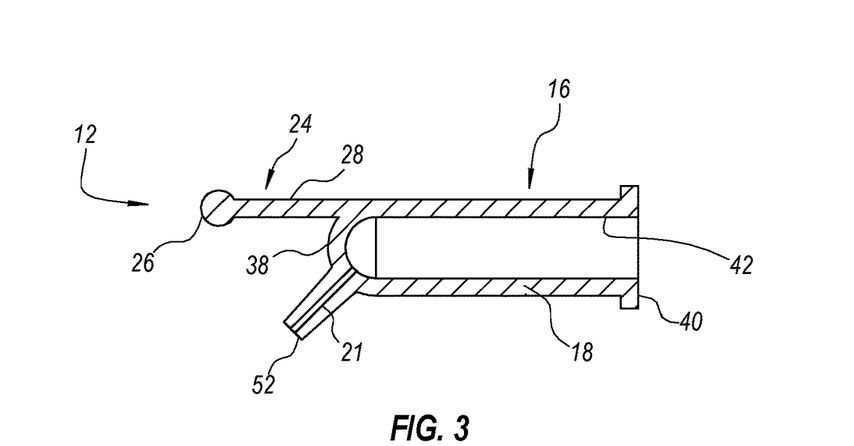
FIG. 3 is a cross-sectional view of the carpule of FIG. 2.

FIG. 1-3 illustrates a carpule 12 comprising a discharging nozzle 20, a burnisher 24, and a barrel 16. The burnisher 24 and the nozzle 20 extend distally from the barrel 16. Burnisher 24 has a working end 26 for burnishing a dental composition. The barrel 16 comprises a tubular body 18 which is elongated from proximal end 40 to distal end 38 to form a longitudinal axis and has a cylindrical chamber 42 with a uniform diameter that allows a plunger (FIG. 9) to be actuated in the chamber 42. Nozzle 20 has a channel 21 that connects chamber 42 to opening 52, which allows composition to be ejected from carpule 12. A cap 32 covers opening 52 when the device is not in use.

Figure 9:
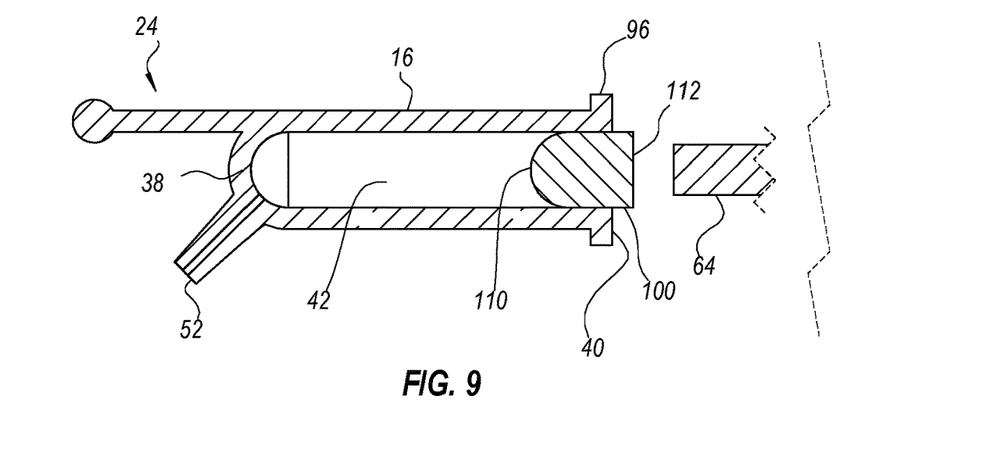
FIG. 9 is a cross sectional view of the carpule of FIG. 1 further illustrating a plunger within the barrel of the carpule and a shaft of the ejector holder for actuating the plunger.

Chamber 42 has a diameter suitable for holding a desired amount of an extrudable dental composition and accommodate the plunger (FIG. 9). The diameter may be at least 1.5 mm, 3 mm, or 6 mm, and/or less than 20 mm, 12 mm, or 8 mm, or within a range of any of the foregoing endpoints. The proximal end 40 is configured to attach to a syringe gun that dispenses the composition by actuating the plunger.

The barrel 16 is configured to hold and dispense various types of extrudable dental materials, such as composites or other similar viscous-type materials that need to be extruded in desired small quantities. Suitable composites typically have a resin, an inorganic filler, and an initiator. Examples of suitable resins include bisphenol A-glycidyl methacrylate (BISGMA), urethane dimethacrylate (UDMA), semi-crystalline polyceram, and the like, or combinations of these. Examples of suitable inorganic fillers includes glass, ceramic, or combinations of these. Examples of suitable initiators include camphorquinone, phenylpropanedione, lucirin, or combinations of these.

The barrel 16 can be preloaded with the dental composition. A preloaded carpule typically includes a removable cap 32 on nozzle 20 and a plunger (FIG. 9) or other seal on proximal end 40 to prevent the composition from curing or drying out. Alternatively, the composition may be prepared separately at the time of use and loaded into the carpule by the practitioner.

The body of the dispensing nozzle 20 may taper inwardly toward discharge opening 52. The opening 52 defined by the orifice may range from at least 0.25, 0.5, 1.0 or larger, and/or less than 2.0, 1.5, 1.25 or smaller, or ranges therebetween, depending upon the flow characteristic of the dental composition. The dispensing nozzle 20 extends from the distal end 38 of the barrel 16 angled relative to the longitudinal axis of the tubular body 18 of the barrel 16. The cap 32 seals the discharging opening 52 and prevents drying of the dental composition.

FIG. 1-3 show the burnisher 24 extending distally from barrel 16 by an elongated shank 28 the supports working end 26. The length of shank 28 and its positioned relative to barrel 16 and nozzle 20 are selected to place the working end 26 a proper distance from opening 52 of nozzle 20. The distance creates a gap between the distal end of nozzle 20 (e.g., opening 52) and the working end 26. Unless otherwise specified, the distance between opening 52 of nozzle 20 and working end 26 of the burnisher 24 is referred to as the working gap 114 (see FIGS. 4-6). The working gap may be at least 3 mm, 5 mm, or 10 mm, and/or less than 12 mm, 15 mm, or 30 mm, or within a range of any of the foregoing endpoints.

The working gap 114 creates the distance from the burnisher necessary for the nozzle to dispense the dental composition without the burnisher interfering with the placement of the composition. Likewise, this working gap 114 distance allows the operator proper space and angles necessary to work the dental composition with the burnisher 24, without the nozzle 20 interfering, when facilitates proper restoration. The working gap 114 can also create proper hand positioning for the operator and minimize hand fatigue. As noted in the summary, that the proper amount of pressure, angle to the dental composition, and time lapsed in the restoration will directly impact the outcome of the tooth restoration.

The position of working end 26 relative to nozzle 20 also depends in part on the length of elongated shank 28. Elongated shank 28 may extend from the distal end 38 of barrel 16 by a distance at least 5 mm, 10 mm, or 15 mm, and/or less than 12mm, 15 mm, or 30 mm, or within a range of any of the foregoing endpoints. The optimal length of the elongated shank will depend on the shape and configuration of the barrel and/or nozzle and can also depend on the particular type of tooth being restored.

Figure 4:
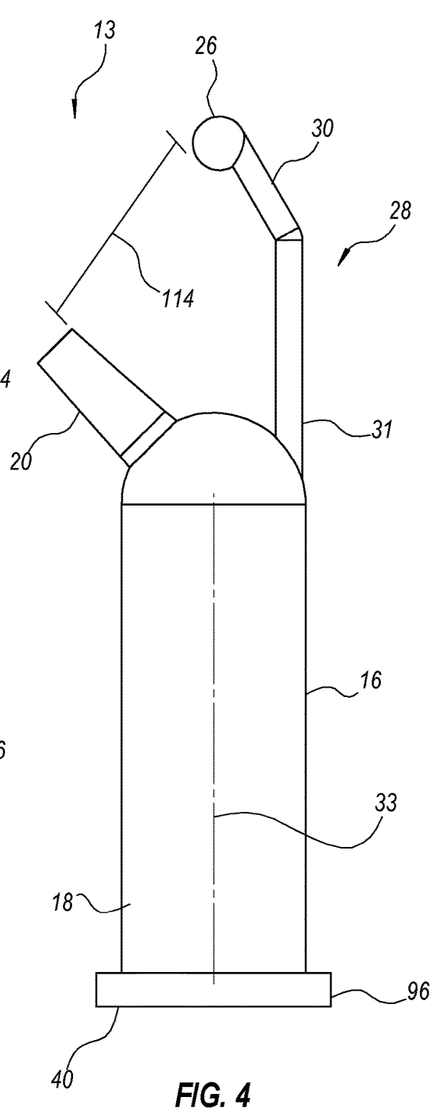
FIG. 4 is an elevational view of a carpule for dispensing and burnishing a dental composition according to a second embodiment of the invention.

The position of working end 26 relative to nozzle 20 can also depend in part on the shape of shank 28. FIG. 4 shows an alternative embodiment of a carpule 13 in which shank 28 includes an angled portion 30 that extends from anterior portion 31 of shaft 28. The angle of the portion 30 relative to the proximal portion of shaft 24 may be at least 5, 15, or 30 degrees, or less than 90, 60, or 45 degrees, or within a range of any of the foregoing degrees. The the foregoing angles may also be measured from longitudinal axis 33.

Figure 6:
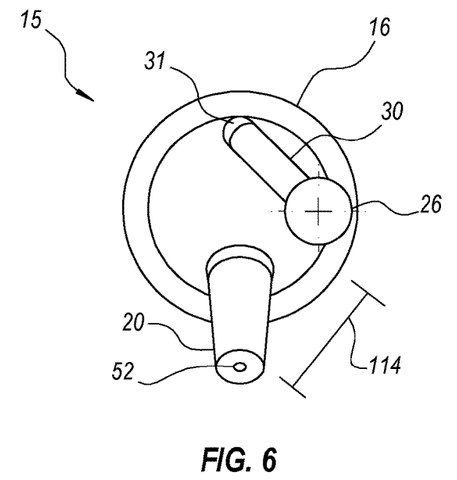
FIG. 6 is a front end view of a carpule according to yet another embodiment of the invention with the burnisher at a lateral angle.

The angled portion of shaft 30 of burnisher 24 can have a length of at least 1 mm, 5 mm, or 7 mm, and/or less than 15mm, 10 mm, or 8 mm, or within a range of any of the foregoing endpoints. Carpule 13 also has a spherical working surface that is offset from angled portion 30 (i.e., the center of the sphere is offset from the longitudinal axis of the shaft portion 30. In addition, the angled portion 30 and/or the anterior portion 31 can be angled relative to a horizontal axis 35 or a vertical axis 37 (FIG. 6). The angles may be greater than 5, 10, 15, 30, 45, or 60 degrees, and/or less than 90, 60, 45, or 30, or within a range of the foregoing endpoints.

Angled portion 30 may have a length and a bend in shaft 24 with an angle suitable for the working surface 26 reaching a posterior tooth (i.e., back of the mouth). Configuring the carpule for placement in the back of the mouth can be advantageous since these types of restorations tend to be more difficult and space constrained as compared to the compared to the anterior area of the mouth. If the working end 26 is not angled correctly, the back of the mouth can be quite difficult for the practitioner to reach.

Providing a carpule with separate discharging nozzle and burnisher, allows the tools to be used more optimal shapes and sizes as compared to integrating the nozzle and the burnisher. As well as, minimizing time and providing quick accessibility for restoration. This separation, will prevent excess dental composition to be extruded into the restoration site as the burnisher is working the composition. Over extruding the dental composition can cause over-packing, fractures, improper shaping, and weak bonding.

Providing a carpule with a separate burnishing tool and nozzle creates a burnishing tool without a distorted surface and will create a firm and controlled finish on the surface of the composition.

Figure 5:
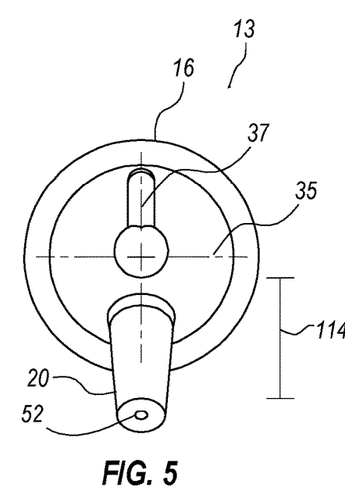
FIG. 5 is a front end view of the carpule of FIG. 4.

The working gap 114 can be configured for a variety of uses and optimized for a variety of ejector holders 54. There can be a variety of working gap 114 distances based on the location of the restoration site and the preference of the operator. The variety of gap distances can be achieved by changing the angle of the elongated shank 28, the working end 26, and the connector shaft 30. As well as changing the placement and length of the burnisher 24 and the nozzle 20. In another embodiment, as shown in FIG. 6, a carpule 15 includes a burnisher 24 extending distally from the barrel 14 and crosses the longitudinal axis of the barrel 14. This placement of the burnisher 24 allows the opening 52 of the nozzle 20 and the working end 26 of the burnisher 24 to be in different vertical planes of each other. FIG. 5 shows an example of an embodiment in which the working end 26 and the opening 52 of the nozzle 20 are in the same vertical plane of each other.

The texture of the working end 26 can be configured to polish and/or remove scratches formed on the dental composition during the dental restoration. The working end of a burnisher is typically rounded, but can be made into various other shapes too. The working end 26 can be pear-shaped, ball-shaped, spoon-shaped, oval-shape, acorn-shaped, beavertail-shaped, cone-shaped, oblong-shape, fish tailed shape, football-shaped, cylinder-shape, flat blade-shape. A flat blade shape is commonly used for contouring composites to a flat tooth surface. Ball-Shape resembles a ball and can be used to pack the dental composition. It can also be used to probe and find specific orodontal margins. A burnisher that resembles a beaver's tail in shape has a broad, flat blade, is smoothly continuous with the shank, meeting it in a slight curve; the edges and the point are smoothly rounded. Beavertail smooths and burnishes lingual and facial composition walls. The football shaped burnisher smooths, contours, and condenses the dental material. The acorn shape burnisher also smooths and can create occlusal anatomy. T-ball shaped burnisher functions to smooth, contour, and initiate carving. The preferred shape of the working end 26 is ball-shape and is generally optimal for compacting, smoothing or working the dental composition injected by the dental device 10. Each shape can be made in a variety of sizes. The variety of shapes and sizes allows the practitioner to select the correct instrument that is optimal for the particular area and tooth surface.

The surface of working end 26 of burnisher 16 is typically smooth but can be textured such as smooth, abrasive, adhesive, and nodular or any suitable for working the dental composition. A serrated texture may be used to pack or condense the dental composition whereas a smooth texture may be used to polish the dental composition.

In one embodiment, the working end 26 of the burnisher is transparent. A transparent end allows for light transmission and thereby providing the curing of composite materials while retaining the burnisher on the working surface of the tooth. This configuration may be useful when a practitioner needs to maintain resistance against the tooth surface and the dental composition to maximize the contouring results during the curing process.

The body of the barrel 16, the nozzle 20, and the burnisher 24 can be molded as a single injection molded part. In addition, portions of the barrel 16, nozzle 20 and burnisher 24 can be molded form a single injection molded part.

In an alternative embodiment, the connecting shaft 30 and working end 26 can be removed and disconnect from the elongated shank 28. The operator can remove and replace the working end of the burnisher. Thus, allowing the operator to specifically choose a correct size, shape, or length of the working end for the restorative site. The exchange of working ends can be achieved by using any suitable connector. The connection may be keyed to allow only one particular orientation for connection. The connection can be any connection suitable for maintaining rigidity under the forces used during burnishing, including, but not limited to snap connect, press fit, fastener, bayonet, luer lok, and the like.

As mentioned, the proximal end 40 of carpule 12 may be configured to receive a plunger from an ejector holder or dental gun. The carpule may have any connector known in the art for connecting to a syringe. FIGS. 1-3 provide a non-limiting example of a connection mechanism. The proximal end of the barrel has a flange 96 or lip which will provide a holding ledge 95 for the ejector holder prior to use. The holding ledge 95 has a height range at least 0.2 mm, 0.5 mm, or 1 mm, and/or less than 2 mm, or 3 mm, or within a range of any of the foregoing endpoints. The length of the barrel at a length at least 8 mm, 15 mm, or 20 mm, and/or less than 22 mm, 30 mm, or 50 mm, or within a range of any of the foregoing endpoints.

FIG. 5 illustrates a side elevation of one non-limiting example of an ejector holder 54 designed to hold in operative position a carpule 12 embodying the present invention. The ejector holder 54 comprises a tube 56 having an interior bore 58 extending from the rearward end 60 of the tube 56 toward the forward end 62 and configured to receive a plunger driver 44 of the same diameter as that of the interior bore 58. For the major portion of the length of the plunger 44, the forward end of the plunger may have a smaller diameter extension 64.

The rearward end 60 of the tube 56 extends through and is fixed to a handle member 46 with which the tube 56 is perpendicular. Pivotally connected to the handle 46 is an operating lever 66, the upper end of which is pivotally connected to the upper end of handle 46 by a pivot pin 68. The upper end 70 of operating lever 66 is offset laterally to facilitate operation of the lever 66 with respect to the outer end of plunger 44 which terminates in a button 72 engageable by the inner surface 74 of operating lever 66.

The forward end 62 of the tube 56 may be tapered and is provided with a longitudinally extending opening comprising compartment 76 which extends rearward from the terminal end of the forward end 62 toward the interior bore 58. The lower surface of compartment 76, is semi-cylindrical and is complementary to the elongated body of carpule 12 so as to receive it. However, the sidewalls 78 and 80 of compartment 76 extend upwardly from the semi-cylindrical bottom surface shown in FIG. 6 and are parallel to each other for a limited distance and the upper edges 82 and 84 extend toward each other a limited distance. The uppermost portions of sidewalls 82 and 84 also have limited flexibility, whereby the distance between the upper edges 82 and 84 of the sidewalls 78 and 80, is slightly less than the diameter of the carpule 12, whereby there is a snapping action retaining function provided by sidewalls 78 and 80, and the upper edges 82 and 84, with respect to the carpule 12 when the latter is inserted in the compartment 76.

Tube 56, handle member 46, and operating lever 66 may be formed in a rigid plastic material in order that these elements may be formed readily and accurately by molding from raw plastic material; obviously, the coiled spring 94 is formed from spring wire for purposes of retracting the plunger 44 when the operating lever 66 is released, following an ejection of the dental material from the carpule 12.

Figure 7:
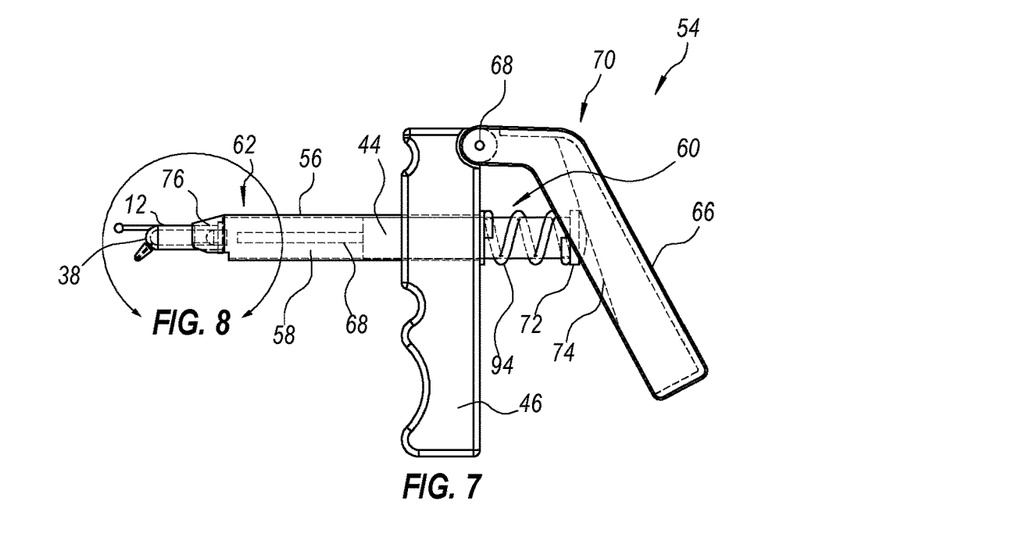
FIG. 7 illustrates a side elevation of a dental device including an ejector holder with the carpule of FIG. 1 positioned therein.
Figure 8:
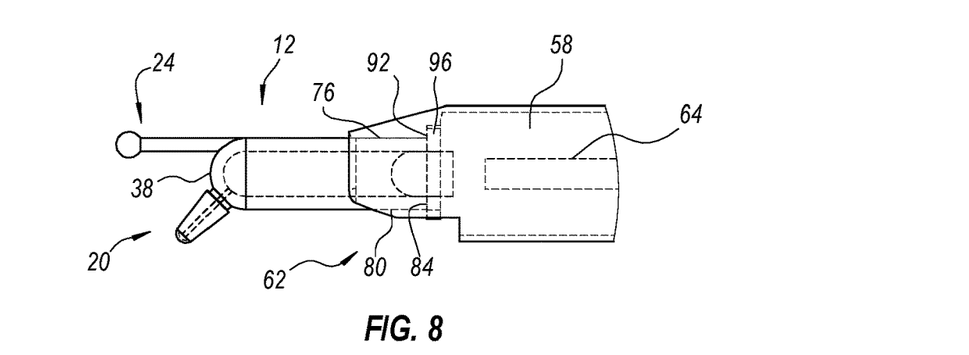
FIG. 8 is a sectional view of the dental device of FIG. 7.

To eject the dental material from the nozzle 20, the carpule 12 includes a piston 100, which is very closely complementary in diameter to the interior of the carpule 12, and distal end 110 thereof also is hemi-spherical and complementary to the distal end 38 of the carpule 12. The outer end 112 of the piston may be flat for engagement, for example, with the extension 64, shown fragmentarily in FIG. 7, when the plunger 44 is moved forwardly by actuation of the operating lever 66.

Removal of the carpule 12 from the compartment 76 is accomplished readily by snapping the carpule outwardly beyond the somewhat flexible upper edges 82 and 84 of the compartment 76 after the contents within the cartridge have been discharged or exhausted.

Ejector 54 may be very simple to permit sure and quick mounting and removal of the carpule within the compartment. The carpule can be filled at a factory with predetermined quantities of material, by automatic machinery. The carpule 12 can be disposable or refillable.

The present invention also relates to methods for restoring a dental composition using the carpules described herein. After the decay is removed from a tooth and the site is prepared and dried for tooth restoration, a dental device as described in this application can be used to fill and restore the tooth. For example, a carpule 12, filled with a particular dental composition, is attached to the ejector holder 50. The practitioner can then dispense, through the nozzle, the dental composition into the site where the decayed tooth was removed. The practitioner can then rotate his or her wrist and place the working end of the burnisher into the composition without removing the carpule from the patient's mouth. The practitioner can then press and smooth the composition against the edges of the tooth as well as compact the composition. The practitioner can continue filling and compressing until the cavity is filled. Excess composition can be removed using the burnisher tool. Once the cavity is filled and compacted, the burnisher can be used to remove excess composition and to smooth and shape the composition. If needed, a working head may be replaced during the procedure to provide differently shaped working heads for completing certain aspects of working the composition. The methods of carrying out a restoration may also include initiating curing of the dental composition. In some embodiments, curing the dental composition includes in part using a UV curing light.

Figure 10:
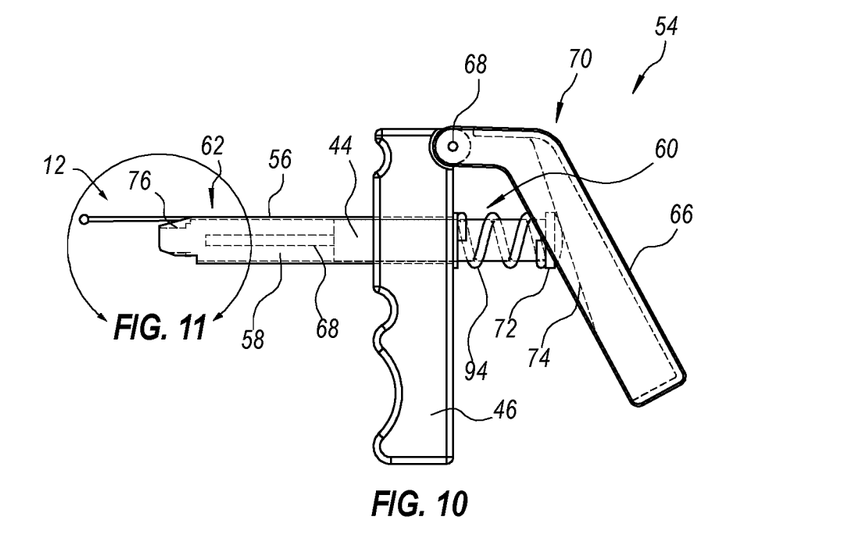
FIG. 10 illustrates a side elevation of the ejector holder of FIG. 7 with the burnisher of the carpule of FIG. 1 attached to the ejector holder.
Figure 11:
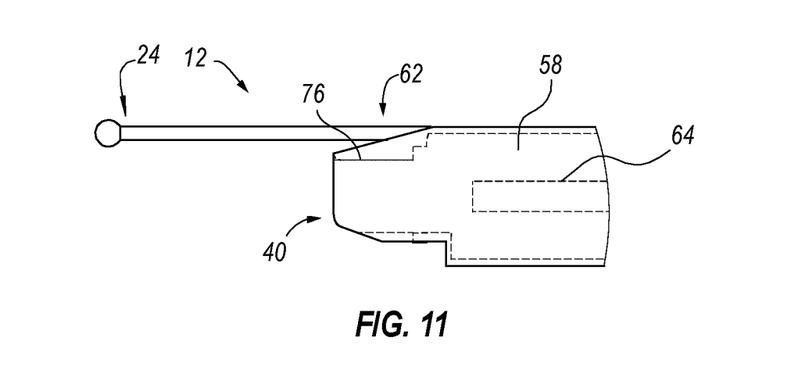
FIG. 11 is a sectional view of the ejector holder of FIG. 10.

In another embodiment, a burnisher as described in any of the foregoing embodiments may be integrally or removably attached to an ejector holder 54 and extended beyond or adjacent to carpule 12 to allow for burnishing without removing carpule 12. FIGS. 10 and 11 illustrate a burnisher 24 connected to ejector holder 50. Burnisher 24 is connected to holder 50 so as to allow a carpule 12 to be placed therein and ejected with holder 50. Burnisher 24 is positioned on holder 24 to allow for burnishing after placement of a dental composition. Burnisher 24 can have lengths, bends, shapes, sizes, etc. as described above, but additionally the burnisher is offset from the longitudinal axis of the carpule (as compared to positions described above) by an amount that allows attachment of the burnisher to or near the distal end of holder 50. The burnisher 24 may be adhered to the holder 50, press fitted, snap fitted, or connected using any other suitable means for attachment. Alternatively, burnisher 24 may be an integral piece of the housing of holder 50. For instance, burnisher 24 may be injected molded as a single piece with one or more structures of the ejector holder providing support for carpule 12.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

I claim:

1. A dental device for dispensing and working a dental composition, comprising:
    a carpule including a barrel, a nozzle, and a burnisher, wherein:
        the barrel has a cylindrical interior chamber adapted to receive the dental composition;
        the nozzle has a proximal end in fluid communication with the barrel and a distal end configured to dispense the dental composition;
        the burnisher has an elongated shank with a working end configured to work the dispensed dental composition; and
        at least a portion of the burnisher extends adjacent to the nozzle so as to provide a gap between the distal end of the dispensing nozzle and the working surface of the burnisher.

2. The dental device as in claim 1, wherein the gap between the working surface of the burnisher and the distal end of the nozzle is in a range from 7 mm to 15 mm.

3. The dental device as in claim 1, wherein the working end of the burnisher has a shape selected from the group consisting of pear-shaped, ball-shaped, flathead-shaped, spoon-shaped, oval-shape, acorn-shaped, beavertail-shaped, cone-shaped, blade-shaped, and oblong-shape.

4. The dental device as in claim 1, wherein the working end of the burnisher has a texture selected from the group smooth, abrasive, adhesive, and nodular.

5. The dental device as in claim 1, further comprising the dental composition disposed within the barrel.

6. The dental device as in claim 5, wherein the dental composition is a composite comprising a resin, an inorganic filler, and an initiator.

7. The dental device as in claim 6, wherein:
    the resin comprises bisphenol A-glycidyl methacrylate (BISGMA), urethane dimethacrylate (UDMA), semi-crystalline polyceram, or combinations thereof
    the inorganic filler include a glass, a ceramic, or a combination thereof and
    the initiator includes camphorquinone, phenylpropanedione, lucirin, or a combination thereof.

8. The dental device of claim 1, further comprising an ejector holder including a plunger.

9. The dental device as in claim 8, wherein the ejector holder includes a spring loaded plunger, a moveable handle, and a housing that holds the dental carpule.

10. The dental device as in claim 1, wherein at least a portion of each of the burnisher, barrel, and nozzle are integrated into a single body of material.

11. The dental device as in claim 10, wherein the single body of material is an injection molded part.

12. The dental device as in claim 11, wherein the single body of material includes the working end of the burnisher.

13. The dental device as in claim 1, wherein the elongated shaft includes a releasable connector for selectively switching between different working end.

14. The dental device as in claim 1, wherein the elongated shaft has an angled portion that creates a bend in the shaft.

15. The dental device as in claim 14, wherein the angle is in a range from 15-60 degrees.

16. The dental device as in claim 1, wherein the burnisher extends distally from the distal end of the barrel by 5 mm to 20 mm.

17. The dental device as in claim 1, wherein the elongated shank of the burnisher extends from a distal portion of the tip at an angle in a range of 0 degrees to 45 degrees relative to a longitudinal axis of the nozzle.

18. The dental device as in claim 1, wherein the working end of the burnisher is transparent.

19. A method for dispensing and working a dental composition, comprising:

providing a dental device as in claim 1, the dental device having a dental composition and a plunger disposed in the barrel thereof, wherein the plunger is proximal to the dental composition within the barrel;

positioning the dispensing tip within a mouth and ejecting the dental composition using the plunger; and after the dental composition is ejected and prior to removing the dispensing tip from the mouth, working the ejected composition using the working end of the burnisher.

20. The method as in claim 19, further comprising initiating curing of the dental composition.

21. The method as in claim 20, wherein the curing is initiated with a UV curing light.

\* \* \* \* \*